US00PP17366P2

(12) United States Plant Patent
Joergensen

(10) Patent No.: US PP17,366 P2
(45) Date of Patent: Jan. 16, 2007

(54) ***ARGYRANTHEMUM* PLANT NAMED 'DANSUN'**

(50) Latin Name: *Argyranthemum frutescens*
Varietal Denomination: Dansun

(75) Inventor: Kaj Joergensen, Aarslev (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/146,242

(22) Filed: Jun. 6, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Argyranthemum* plant named 'Dansun', characterized by its compact, upright and rounded plant habit; freely branching habit; dense and bushy plant habit; freely flowering habit with numerous inflorescences per plant; and large daisy-type inflorescences with bright yellow-colored ray florets and golden yellow-colored disc florets.

1 Drawing Sheet

Botanical designation: *Argyranthemum frutescens.*
Cultivar denomination: 'Dansun'.

BACKGROUND OF THE INVENTION

The present invention relates to a new and distinct cultivar of *Argyranthemum* plant, botanically known as *Argyranthemum frutescens* and hereinafter referred to by the cultivar name 'Dansun'.

The new *Argyranthemum* is a naturally-occurring whole plant mutation of the *Argyranthemum frutescens* cultivar Tanja, not patented. The new *Argyranthemum* was discovered and selected as a single plant from within a population of plants of the cultivar Tanja in a controlled environment in Aarslev, Denmark in 1999.

Asexual reproduction of the new *Argyranthemum* by terminal cuttings in a controlled environment in Aarslev, Denmark since 2000, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Dansun' and distinguish the new *Argyranthemum* as a new and distinct cultivar:

1. Compact, upright and rounded plant habit.
2. Freely branching habit, dense and bushy plants.
3. Freely flowering habit with numerous inflorescences per plant.
4. Large daisy-type inflorescences with bright yellow-colored ray florets and golden yellow-colored disc florets.

Plants of the new *Argyranthemum* differ from plants of the parent, the cultivar Tanja in the following characteristics:

1. Plants of the new *Argyranthemum* are more compact than plants of the cultivar Tanja.
2. Plants of the new *Argyranthemum* are more freely branching than plants of the cultivar Tanja.
3. Plants of the new *Argyranthemum* have stronger leaves than plants of the cultivar Tanja.
4. Plants of the new *Argyranthemum* have larger inflorescences than plants of the cultivar Tanja.

Plants of the new *Argyranthemum* can be compared to plants of the cultivar Lemon Delight, disclosed in U.S. Plant Pat. No. 11,774. In side-by-side comparisons conducted in Encinitas, Calif., plants of the new *Argyranthemum* were more compact, had smaller leaves and larger inflorescences than plants of the cultivar Lemon Delight. In addition, plants of the new *Argyranthemum* and the cultivar Lemon Delight differed in ray floret coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum.*

The photograph at the top of the sheet comprises a side perspective view of typical flowering plants of 'Dansun' grown in a container.

The photograph at the bottom of the sheet comprises a close-up view of typical inflorescences of 'Dansun'.

DETAILED BOTANICAL DESCRIPTION

The aforementioned photographs, following observations and averaged measurements describe plants grown in Encinitas, Calif., in an outdoor nursery under full sunlight during the spring and summer with day temperatures averaging 24° C., night temperatures averaging ranging from 19° C. and light levels about 4,000 foot-candles. Plants were grown in 15-cm containers. Plants had been growing for about 15 weeks when the photographs and description were taken. Color references are made to The Royal Horticultural Society Colour Chart, 1995 Edition, except where general terms of ordinary dictionary significance are used.

Botanical classification: *Argyranthemum frutescens* cultivar Dansun.

Parentage: Naturally-occurring whole plant mutation of the *Argyranthemum frutescens* cultivar Tanja, not patented.

Propagation:

*Type.*—Terminal vegetative cuttings.

*Time to initiate roots.*—About 12 days at 20° C.

*Time to produce a rooted cutting.*—About 18 to 20 days at 20° C.

*Root description.*—Fibrous, fine; white in color.

*Rooting description.*—Freely branching; dense.

Plant description:

*General appearance.*—Inverted triangle; compact, upright and rounded plant form with dense foliage and inflorescences held above and beyond the foliage. Moderately vigorous growth habit.

*Plant height.*—About 22 cm.

*Plant width.*—About 28 cm.

*Lateral branch description.*—Quantity per plant: About four primary lateral branches, each with about seven or eight secondary lateral branches. Length: About 15 to 18 cm. Diameter: About 8 mm. Internode length: About 5 mm. Aspect: Initially upright to outwardly spreading. Texture: Smooth, glabrous. Strength: Strong. Color: 145B.

*Foliage description.*—Arrangement: Alternate, simple. Length: About 5.5 cm. Width: About 4.7 cm. Shape: Pinnatifid, deeply and irregularly dissected. Apex: Broadly acute. Base: Attenuate. Margin: Entire; deeply and finely dissected; sinuses parallel. Texture, upper and lower surfaces: Smooth, glabrous. Venation pattern: Pinnate. Petiole length: About 2.3 cm. Petiole diameter: About 4 mm. Petiole texture, upper and lower surfaces: Smooth, glabrous. Color: Developing foliage, upper and lower surfaces: 138A. Fully expanded foliage, upper surface: 147A; venation, 147A. Fully expanded foliage, lower surface: 147B; venation, 144B. Petiole, upper surface: 146B. Petiole, lower surface: 146C.

Inflorescence description:

*Appearance.*—Large daisy-type inflorescences with ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plant flower from spring to early fall in Southern California; plants flower continuous during this period.

*Inflorescence longevity.*—Inflorescences last about seven to ten days on the plant.

*Quantity of inflorescences.*—Freely flowering, about five open inflorescences and inflorescence buds per lateral branch.

*Fragrance.*—Sour.

*Inflorescence size.*—Diameter: About 5.7 to 6 cm. Depth (height): About 2 cm. Diameter of disc: About 1.5 cm. Receptacle height: About 6 mm. Receptacle diameter: About 1.7 cm.

*Inflorescence buds, at stage of showing color.*—Height: About 1.3 cm. Diameter: About 1 cm. Shape: Ovoid. Color: 5A.

*Ray florets.*—Quantity per inflorescence: About 22 arranged in a single whorl. Shape: Ligulate. Length: About 3 cm. Width: About 8 mm. Apex: Emarginate. Base: Acute. Margin: Entire. Texture, upper and lower surfaces: Smooth, glabrous; velvety. Aspect: Initially upright, with development, eventually horizontal to the peduncle. Color: When opening, upper surface: 6A. When opening, lower surface: 6D. Fully opened, upper surface: 5B to 5C. Fully opened, lower surface: 5D.

*Disc florets.*—Arrangement: Massed at the center of the inflorescence. Quantity per inflorescence: Numerous, about 250. Shape: Tubular, elongated; apex, five-pointed; base, fused. Length: About 6 mm. Diameter, apex: About 2 mm. Diameter, base: Less than 1 mm. Color: Immature: 14A. Mature, apex: 14A. Mature, mid-section: 155A. Mature, base: 145C.

*Involucral bracts (phyllaries).*—Appearance: Scale-like; margins, papery. Quantity per inflorescence: About 48; imbricate. Length: About 3 mm. Width: About 1.5 mm. Shape: Elliptic. Apex: Acute. Base: Truncate. Margin: Entire. Texture, upper and lower surfaces: Smooth, glabrous. Color, upper surface: 145C. Color, lower surface: 143C.

*Peduncle.*—Strength: Moderately strong; wiry. Aspect: Upright to about 45° from vertical. Length, terminal inflorescence: About 8.3 cm. Length: second inflorescence: About 5 cm. Diameter: About 2 mm. Texture: Smooth, glabrous. Color: 144A.

*Reproductive organs.*—Androecium: Only on disc florets. Stamen quantity per floret: Five. Anther size: About 1.5 mm to 2 mm. Anther shape: Oval to elongate. Anther color: 14A. Amount of pollen: Scarce. Pollen color: 14A. Gynoecium: Present on ray and disc florets. Pistil quantity per floret: One. Pistil length: About 6 mm. Stigma shape: Two-parted. Stigma color: 12A. Style length: About 3 mm. Style color: 12C. Ovary color: 4D.

*Seed/fruit.*—Seed and fruit production has not been observed.

Disease/pest resistance: Resistance to pathogens and pests common to *Argyranthemums* has not been observed on plants grown under commercial conditions.

Temperature/weather tolerance: Plants of the new *Argyranthemum* have been observed to be tolerant to rain, wind and to temperatures from 0 to 30° C.

It is claimed:

1. A new and distinct cultivar of *Argyranthemum* plant named 'Dansun', as illustrated and described.

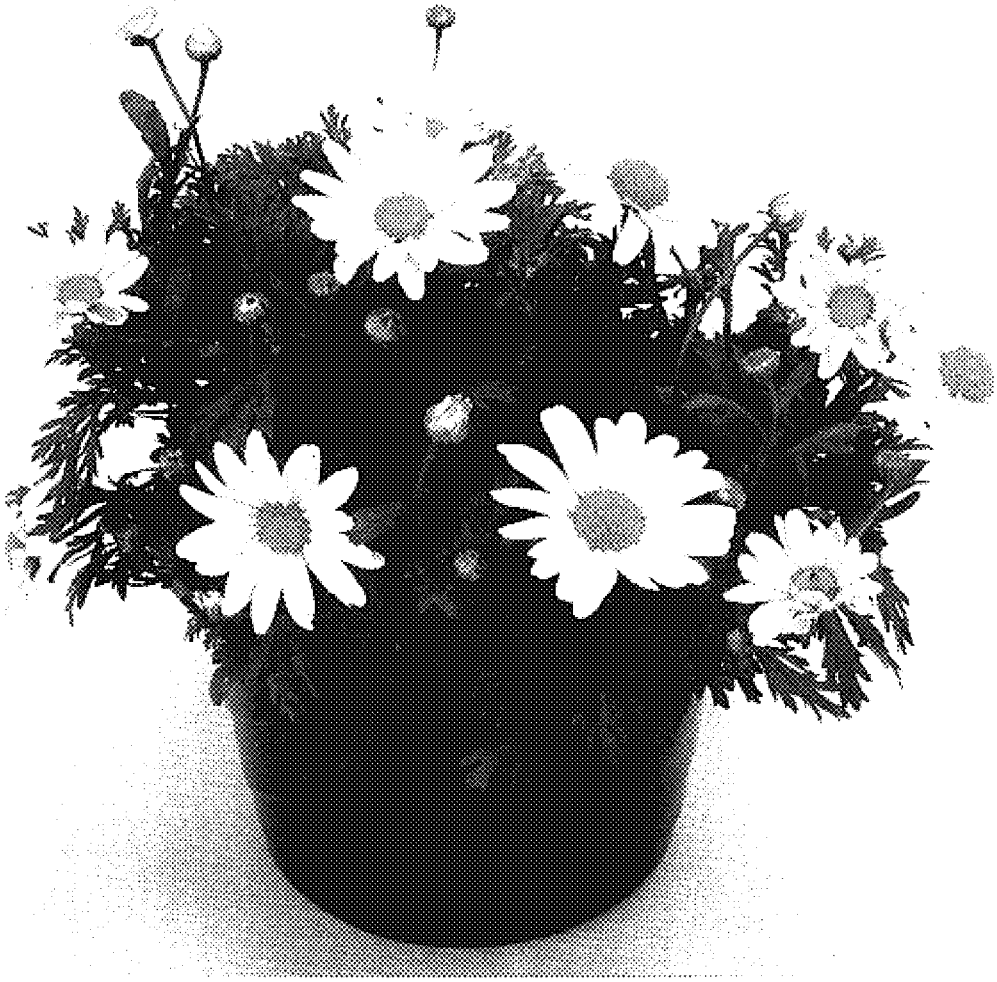
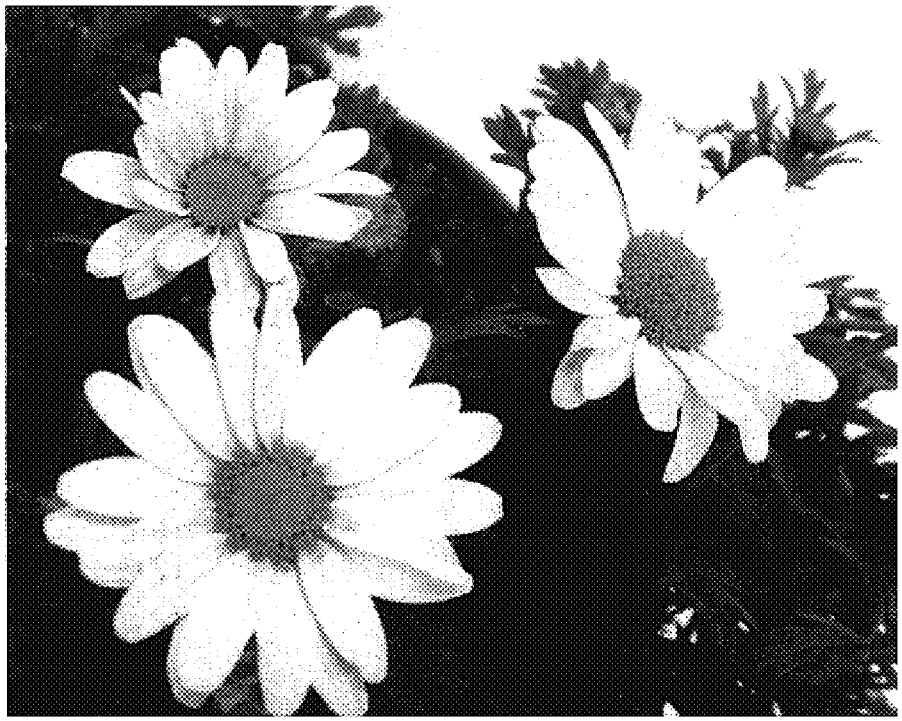

* * * * *